(12) United States Patent
Levine

(10) Patent No.: US 8,262,306 B2
(45) Date of Patent: Sep. 11, 2012

(54) DISPENSER AND APPLICATOR THAT BRING REACTIVE SUBSTANCES INTO CONTACT WITH EACH OTHER AT TIME OF USE

(75) Inventor: Jonathan B. Levine, Purchase, NY (US)

(73) Assignee: JBL Radical Innovations, LLC DE (US)

( * ) Notice: Subject to any disclaimer, the term of this patent is extended or adjusted under 35 U.S.C. 154(b) by 678 days.

(21) Appl. No.: 12/407,013

(22) Filed: Mar. 19, 2009

(65) Prior Publication Data
US 2010/0240013 A1 Sep. 23, 2010

(51) Int. Cl.
*B46M 11/06* (2006.01)

(52) U.S. Cl. ............... 401/183; 401/186; 401/143

(58) Field of Classification Search .......... 401/183–186, 401/145; 222/92, 206, 212; 403/88–89; 604/3, 290
See application file for complete search history.

(56) References Cited

U.S. PATENT DOCUMENTS

| | | | |
|---|---|---|---|
| 4,279,527 A | 7/1981 | Moe et al. | |
| 4,748,990 A | 6/1988 | Brown et al. | |
| 5,509,744 A | 4/1996 | Frazier | |
| 5,693,313 A | 12/1997 | Shiraishi et al. | |
| 5,857,796 A | 1/1999 | Waldmann | |
| D413,730 S | 9/1999 | Frazier | |
| D416,389 S | 11/1999 | Frazier | |
| 6,254,297 B1 | 7/2001 | Frazier | |
| 6,592,282 B2* | 7/2003 | Fontanet et al. | 401/266 |
| 6,623,272 B2 | 9/2003 | Clemans | |
| 6,648,904 B2 | 11/2003 | Altshuler et al. | |
| 6,726,482 B2 | 4/2004 | Atkins et al. | |
| 6,755,586 B1 | 6/2004 | Frazier | |
| D495,843 S | 9/2004 | Frazier | |
| D504,775 S | 5/2005 | Frazier | |
| 6,902,397 B2 | 6/2005 | Farrell et al. | |
| 6,908,607 B2* | 6/2005 | Banerjee et al. | 424/53 |
| 6,929,475 B1 | 8/2005 | Dragan | |
| 7,004,657 B2 | 2/2006 | Frazier | |
| 7,004,756 B2 | 2/2006 | Andersen | |
| 7,021,848 B1 | 4/2006 | Gruenbacher et al. | |
| 7,070,413 B1 | 7/2006 | Wagner | |
| 7,160,111 B2 | 1/2007 | Baughman | |
| 7,201,577 B2 | 4/2007 | Levine | |
| 7,435,027 B2* | 10/2008 | Hetzel | 401/47 |
| 7,465,119 B2* | 12/2008 | Sogaro | 401/280 |
| 7,597,497 B2* | 10/2009 | Levine | 401/202 |
| 7,740,479 B2* | 6/2010 | Allred et al. | 433/90 |

(Continued)

OTHER PUBLICATIONS

Carol Lewis, "Fighting Gum Disease: How to Keep Your Teeth" US Food and Drug Admin., FDA Consumer magazine, May-Jun. 2001 pp. 1-9.

(Continued)

*Primary Examiner* — David Walczak
*Assistant Examiner* — Jennifer C Chiang
(74) *Attorney, Agent, or Firm* — H. Jay Spiegel

(57) ABSTRACT

A squeezable hermetically sealed vessel contains a whitening compound and an elongated applicator tip extending outwardly from the vessel. A cap closed and seals the applicator tip and the vessel, but may be removed under manual force. Once the cap is removed, the walls of the vessel may be squeezed together to urges the contents of the vessel to flow through a fluid passage through the elongated applicator tip to reach an accommodating surface. The accommodating surface may either be impregnated with a different material that reacts with the contents of the vessel upon contact or covers a chamber that in turn contains such a different material.

40 Claims, 12 Drawing Sheets

U.S. PATENT DOCUMENTS

| | | | |
|---|---|---|---|
| 7,832,956 B2 * | 11/2010 | Ross | 401/269 |
| 7,861,897 B2 * | 1/2011 | Sogaro | 222/209 |
| 2007/0020028 A1 | 1/2007 | Levine | |
| 2007/0122769 A1 | 5/2007 | Levine | |
| 2007/0166666 A1 | 7/2007 | Levine | |
| 2007/0183988 A1 | 8/2007 | Prosise et al. | |
| 2009/0152267 A1 | 6/2009 | May et al. | |

OTHER PUBLICATIONS

Klever, CJ dt al "In vitro tooth whitening by a sodium bicarbonate/peroxide dentifrice" (J. Clin Dent. 1998), pp. 1-2.

* cited by examiner

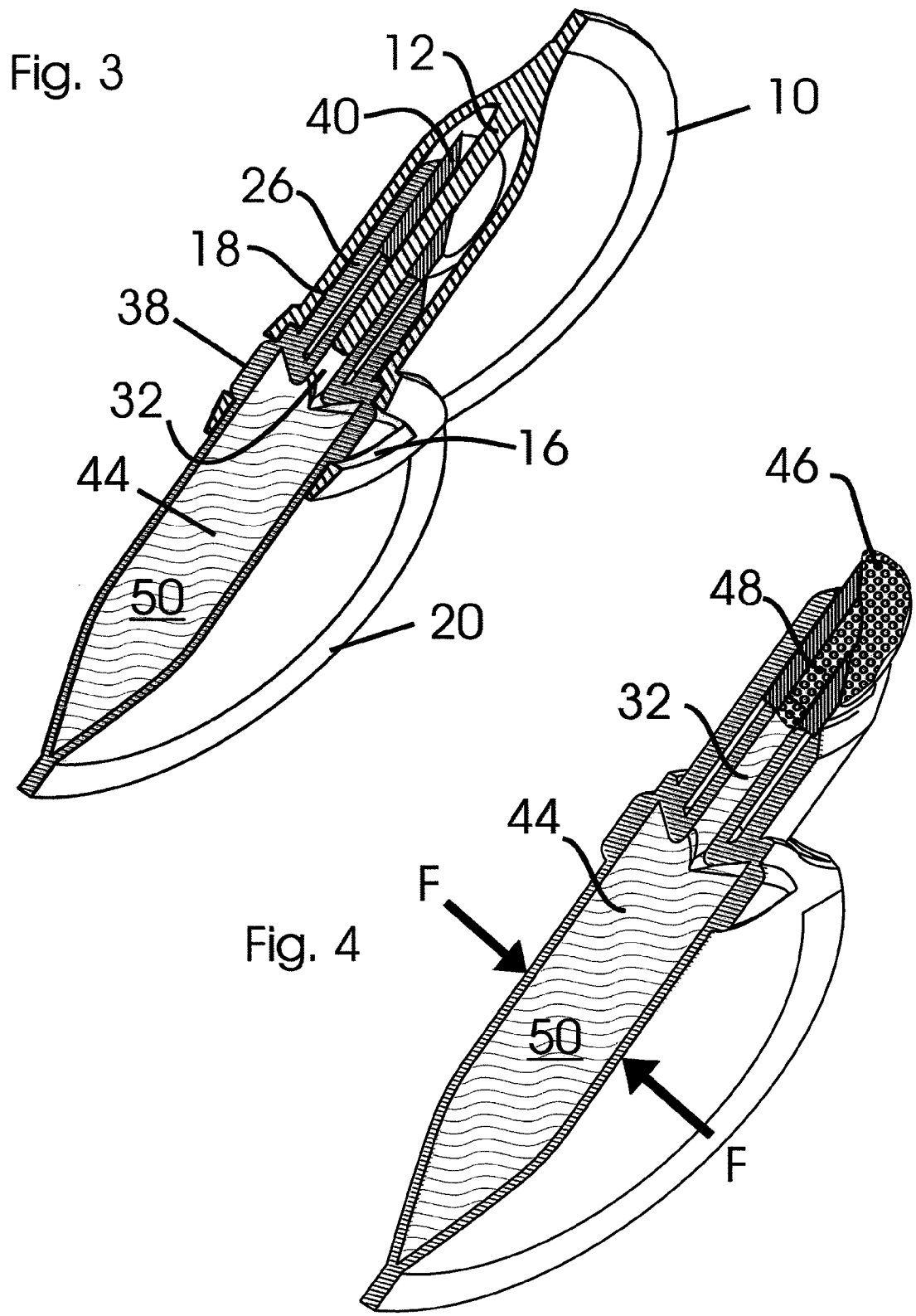

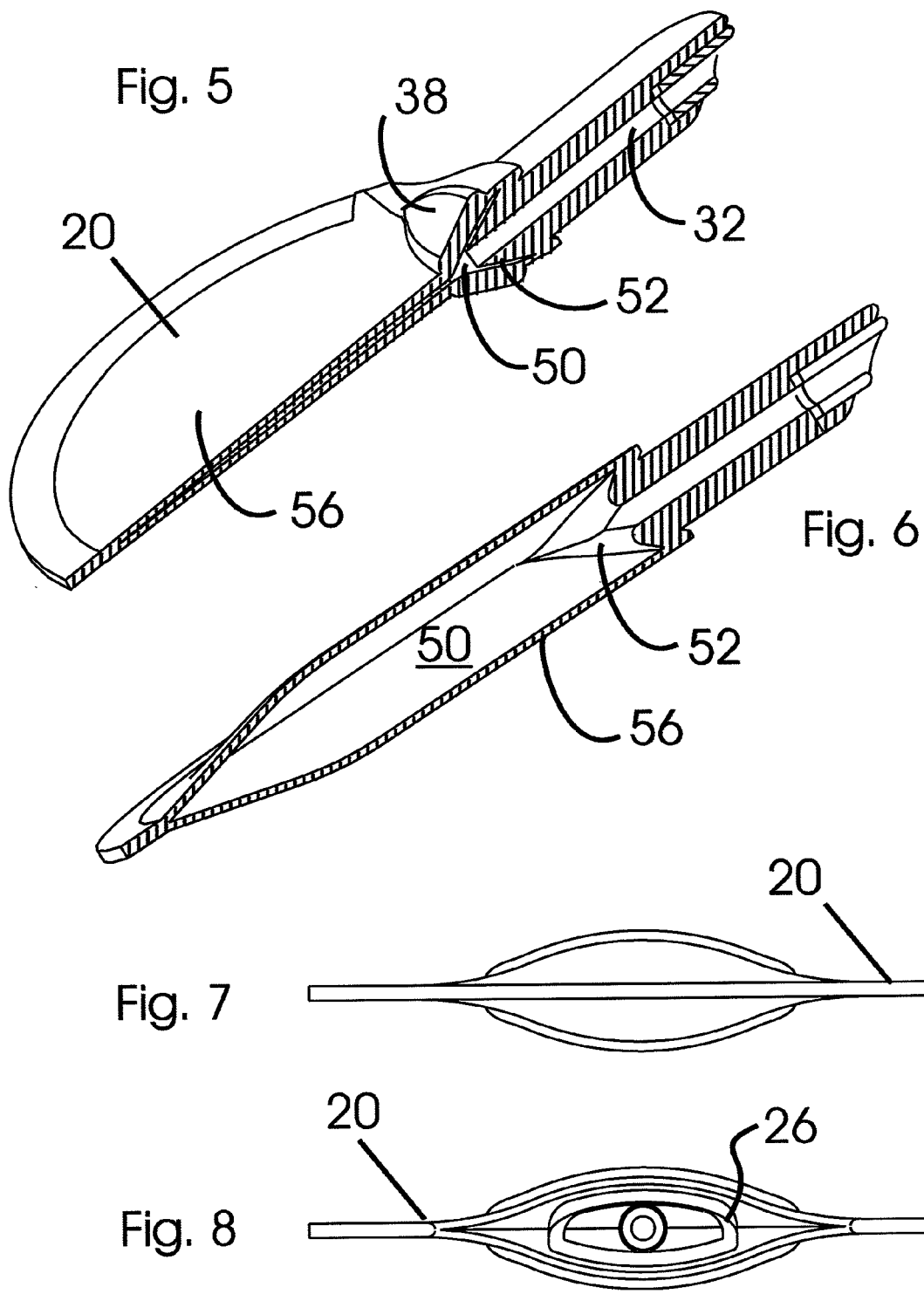

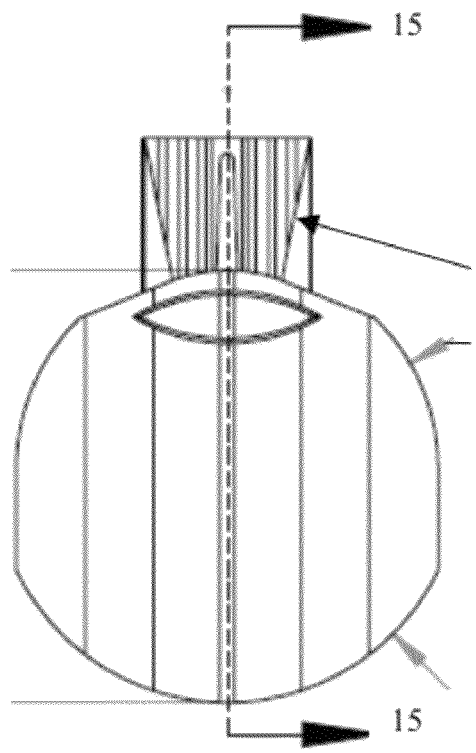
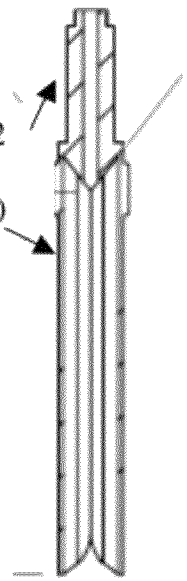
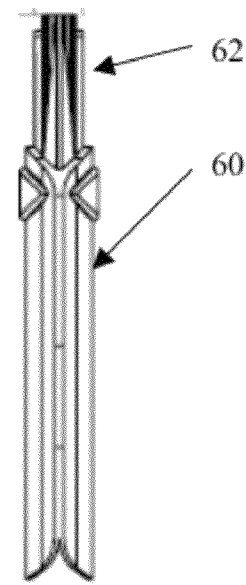
FIG. 14        FIG. 15        FIG. 16
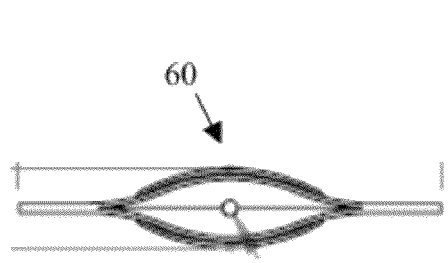
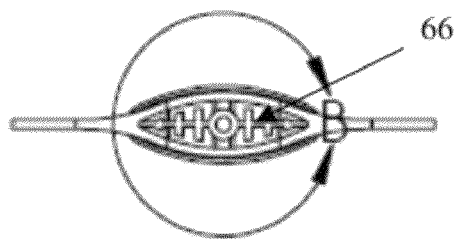
FIG. 17        FIG. 18
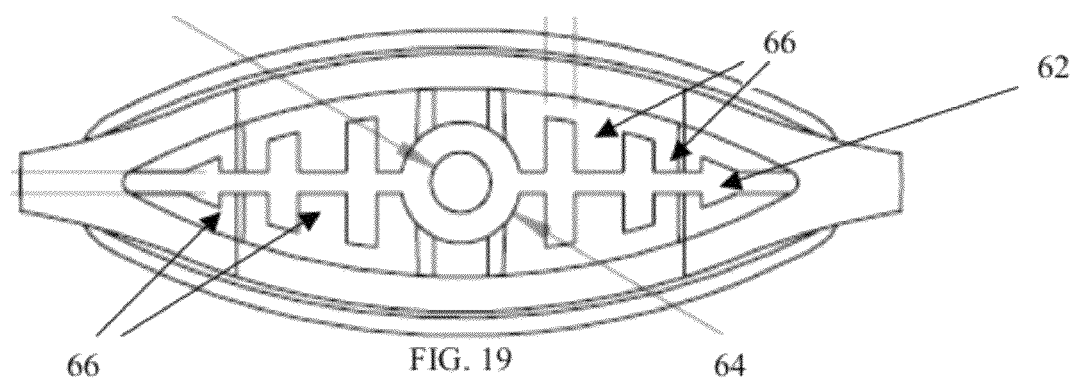
FIG. 19

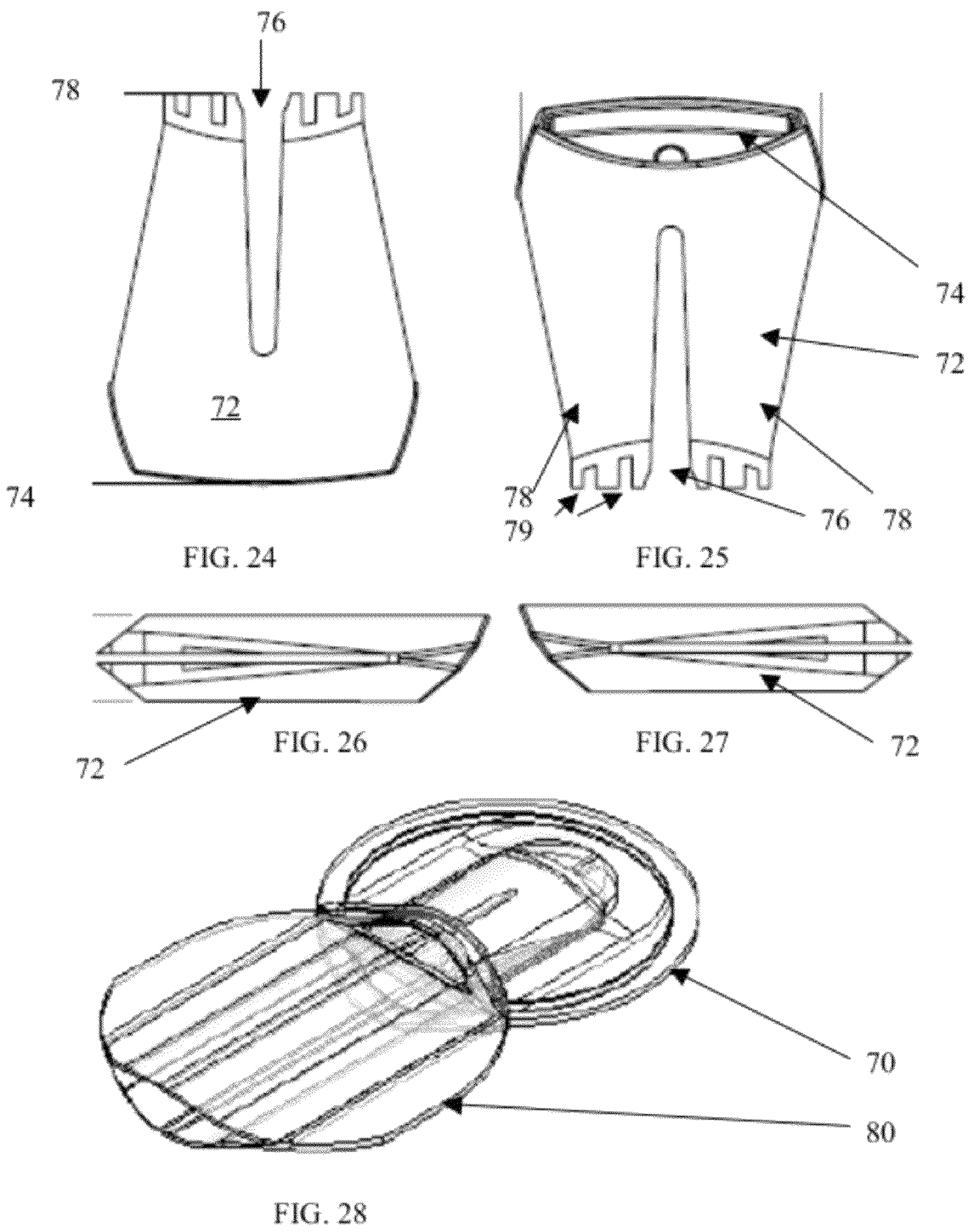

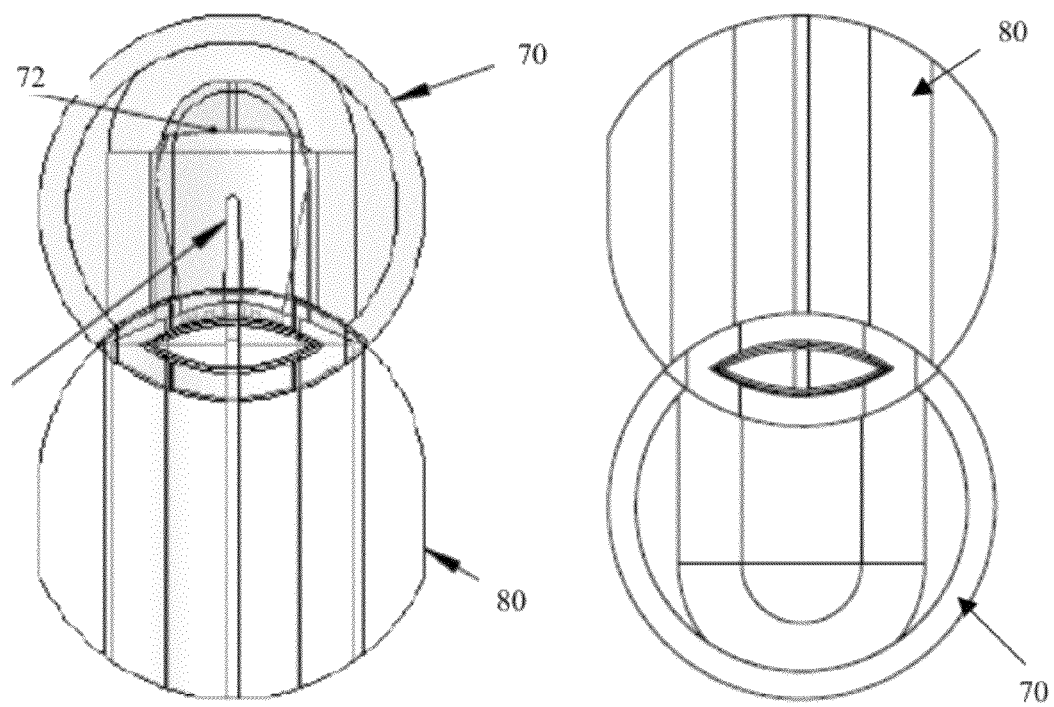
FIG. 29    FIG. 30
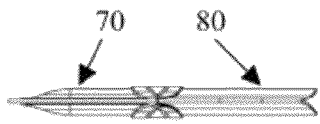      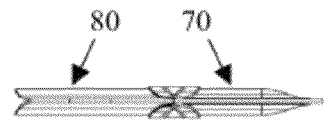
FIG. 31    FIG. 32    FIG. 33

ASSEMBLED READY FOR FILL

HEAT SEALED

TRIMMED / FINISHED PRODUCT

DISPENSER AND APPLICATOR THAT BRING REACTIVE SUBSTANCES INTO CONTACT WITH EACH OTHER AT TIME OF USE

BACKGROUND

1. Field of Invention

The present invention relates to a dispenser and an applicator that leaves two reactive substances separate until time of use. Such uses may include a tooth whitening or polishing system, a treatment for skin and other dermatologic applications, a delivery system for glues or other commercial compounds wherein the substrates are separate until delivery, pharmaceuticals, hemostatic agents, sealants and many other uses. With respect to tooth whitening or polishing in particular, one of the two substances may be hydrogen peroxide and/or carbamide peroxide that is isolated from the other of the two substances, such as sodium bicarbonate. The substances are subsequently mixed together at the time of use, for and during application of the mixture on the targeted surface.

2. Description of Related Art

Peroxide is the active ingredient in many tooth whitening products. There are two types—carbamide peroxide and hydrogen peroxide—both work similarly. The peroxide breaks down into $H_2O$ and a free radical oxygen (a highly reactive oxygen with an unpaired electron), allowing the reactive oxygen to contact the enamel layer of the teeth, thereby oxidizing stain and bleaching the tooth. The reactive oxygen can travel through the enamel of the tooth into the dentinal structure that contains the color pigments. The color pigments are vaporized by the oxidation procedure and thus lightening the overall tooth. Used properly and in safe concentrations, peroxide will not damage the enamel or any other part of teeth Carbamide peroxide breaks down into hydrogen peroxide and urea which then continues to breakdown into ammonia ($NH_3$). Hydrogen peroxide is very unstable and can be stabilized either through formulation, i.e. carbamide peroxide or through a hermetically sealed delivery system such as a strip, a dissolvable film or an ampoule.

A mixture of hydrogen peroxide based whitening compounds with sodium bicarbonate produces notable effervescence in whitening if used immediately after mixing them together. As a result, the efficacy of hydrogen peroxide based whitening compounds is enhanced because of the mixing with the sodium bicarbonate. This is a result of the sodium bicarbonate raising the ph above the threshold of a ph of 9.5 which creates the most reactive perhydroxyl molecule vs. a free radical oxygen formation. The perhydroxyl molecule at the time of use is ideal for tooth whitening as a greater oxidation reaction occurs.

The elements necessary for tooth whitening is the concentration of the hydrogen peroxide and the amount of time the hydrogen peroxide is on the teeth. Teeth whitening systems contain different strengths of peroxide. Those with higher concentrations of peroxide can produce faster, more dramatic whitening of teeth. However, there is an increased risk of creating temporary but uncomfortable tooth sensitivity with the higher concentration formulas. Products with a lower concentration of peroxide carry less risk of unpleasant side-effects, but they do not whiten as quickly as those with higher concentrations. Successful tooth whitening without sensitivity occurs with high frequency of use vs. high concentration of the whitening gel that can cause sensitivity and harm the soft tissues.

Some teeth whitening products are Ph buffered, to reduce the likelihood and severity of side effects of the low ph associated with carbamide peroxide gels. The carbamide peroxide gels can be ph buffered up to a certain amount to reduce the side effects but cannot be packaged higher than a ph of 5.5. for stability reasons. Carbamide peroxide breaks down to hydrogen peroxide combined and urea (an aqueous solution This breaks down even further to $NH_3$ (ammonia) and we don't know the long term consequences of ammonia in the mouth for a long period of time. Carbamide peroxide is found in over-the-counter tray and gel systems and professional tooth whitening tray and gel formulas, light-activated tooth whitening gels and whitening toothpastes. Tooth whitening products containing carbamide peroxide typically range from concentrations of less than 10% to about 22%, which has the equivalent of hydrogen peroxide of 3% and 7.3% respectively. Professional products may contain as much as 35% carbamide peroxide which has an equivalent of 12% hydrogen peroxide. The new whiteners today use hydrogen peroxide in a unique delivery system to avoid the breakdown products, i.e. the ammonia breakdown by-product of the carbamide peroxide gel.

Hydrogen peroxide is found in whitening strips, dissolvable film, and paint on whiteners like an ampoule. These unique delivery systems create a hermetically sealed environment, thus not allowing oxygen in or out keeping the hydrogen peroxide gel stable until used.

Sodium bicarbonate (baking soda) helps clean teeth, freshen breath and neutralize mouth acids that can destroy tooth enamel. Used for decades for dental care, the FDA recognizes it as safe. It has been mixed conventionally with whitening compounds to whiten teeth. It has the effect of raising the ph of tooth whitening gels and creates a highly reactive perhydroxyl molecule.

Magnesium peroxide is recognized as an oxidizer that whitens teeth and aluminum oxide is recognized as a tooth surface polisher.

A need to improve conventional techniques for whitening teeth is discussed in U.S. Pat. No. 7,201,577, U.S. Pat. No. 6,929,475, U.S. Pat. No. 6,726,482 B2 and U.S. Pat. No. 7,070,413.

Various approaches have evolved for at-home teeth whitening procedures (without the need for the dental practitioner). Among the early at-home teeth whitening systems was a paste or gel containing carbamide peroxide that was placed in a dentist administered tray or an over-the-counter boil and bite plastic guard. The gel or paste was applied to tooth surfaces by, for example, the placement of the tray in the mouth, a toothbrush, a cotton swab, etc., as discussed in U.S. Pat. No. 7,070,413.

There are many well-known two-part substrates that, when combined or mixed, form a desired reaction. Such materials may be sealants, adhesives, hemostatic agents, whitening agents, and numerous other equivalent two-part materials that when combined form a material having desired properties, as discussed in U.S. Pat. No. 6,929,475.

U.S. Pat. No. 6,929,475 discloses a single use applicator of chemical or medicament material to be applied to a surface to be treated. The material, which may be a stable, inactive solid powder, is placed on an absorbent portion of the applicator. A liquid activating agent is released onto the absorbent portion of the applicator to activate the otherwise stable, inactive solid powder. The activated powder is applied to surfaces of the tooth with the applicator to whiten and polish the tooth. The absorbent portion may be a cotton swab.

Conventional dispensers that dispense contents from bottles and tubes trap significant amounts of their contents in corner regions. Users therefore, are generally unable to retrieve such trapped contents. Such dispensers may leak if not sealed securely.

It would be desirable to keep two reactants isolated from each other within a dispenser, yet allow them to blend together to form a blended mixture at the time of desired application of the blended mixture to the tooth being treated. It is further desired to apply the blended mixture to the treatment area of the tooth in a direct and even manner of application.

It is also desired to minimize an amount of the contents of the dispenser that cannot be retrieved by a user by preventing the contents from becoming trapped at corners of the dispenser. It is further desired to securely seal the dispenser to prevent leakage.

SUMMARY OF THE INVENTION

The present invention is directed to a tooth whitening and polishing system that does not require a professional, such as a dentist, to provide assistance or application.

The present invention comprises a dispenser that includes a squeezable vessel or fluid container, an applicator tip that defines a fluid passage, a compliant surface at a distal end of the applicator tip, and a cap that closes and seals the applicator tip. A compliant surface is a surface that is yielding or accommodating, as exemplified by foam. The contents of the squeezable vessel or fluid container may be urged out under manual pressure by squeezing together walls of a hollow body of the vessel or fluid container into a flattened condition from a non-flattened condition. The compliant surface may be porous and impregnated with a different material from the contents of the vessel or fluid container, or may cover a chamber that contains such a different material. The applicator tip is elongated to define a length sufficient to reach even deep and hard to reach tooth surfaces to be treated.

As an example, the contents of the vessel or fluid container may be a whitening compound gel whose active ingredient includes hydrogen peroxide or carbamide peroxide. The different material that impregnates the porous compliant surface may be a solid powder such as sodium bicarbonate or baking soda. The porous, compliant surface may be sponge-like. The sodium bicarbonate or baking soda may be in cake form if the porous compliant surface covers a chamber that contains the different material.

When a user squeezes the vessel, its content (e.g., tooth whitening compound gel) passes through (is urged through) the fluid passage to reach the compliant surface where it mixes or blends with the solid powder to preferably produce foam. The foam is applied to the teeth by pressing the compliant surface against the areas of the teeth to be treated and applies the whitening gel, generally, evenly in a squeegee-like manner.

BRIEF DESCRIPTION OF THE DRAWINGS

For a better understanding of the present invention, reference is made to the following description and accompanying drawings, while the scope of the invention is set forth in the appended claims:

FIG. 3 shows a cross-section longitudinally through the filled vessel closed by the cap of FIG. 1.

FIG. 4 shows a cross-section longitudinally through the filled vessel of FIG. 2, without showing the cap.

FIG. 5 shows a cross-section longitudinally of the vessel of FIG. 4 in a flattened condition after squeezing out contents.

FIG. 6 shows a cross-section longitudinally through the vessel for the filled vessel of FIG. 4, without the contents, to allow view of the interior of the vessel.

FIG. 7 shows an end view of the filled vessel of FIG. 4.

FIG. 8 shows an opposite end view of the filled vessel of FIG. 7 to show the applicator tip.

FIG. 14 shows a top plan view of the empty vessel of FIG. 12, also showing section lines 15-15.

FIG. 15 shows a cross section across 15-15 of FIG. 14.

FIG. 16 shows a right side view of the vessel of FIG. 14.

FIG. 17 shows a rear plan of the vessel of FIG. 14.

FIG. 18 shows a front plan view of the vessel of FIG. 14.

FIG. 19 shows a detail view of the portion marked B of FIG. 18.

FIG. 24 shows a top view of the soft, elastomeric application tip of FIG. 21.

FIG. 25 shows a bottom view of the soft, elastomeric application tip of FIG. 21.

FIG. 26 shows a right side view of the soft, elastomeric application tip of FIG. 21.

FIG. 27 shows a left side view of the soft, elastomeric application tip of FIG. 21.

FIG. 28 is an isometric view of a dispenser that includes a cap closing the vessel of FIGS. 11 and 13.

FIG. 29 is top view of the dispenser of FIG. 28.

FIG. 30 is bottom view of the dispenser of FIG. 28.

FIG. 31 is a right side view of the dispenser of FIG. 28.

FIG. 32 is a front view of the dispenser of FIG. 28.

FIG. 33 is a left side view of the dispenser of FIG. 28.

DETAILED DESCRIPTION OF THE PREFERRED EMBODIMENT

Figure 1:
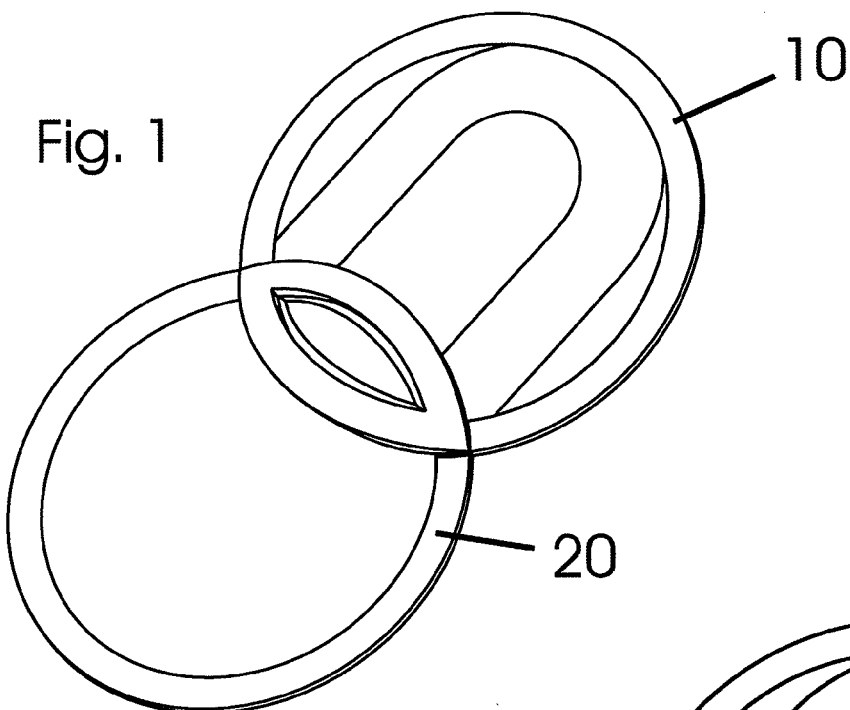
FIG. 1 shows an isometric view of the dispenser of the present invention with a filled vessel closed by a cap.
Figure 2:
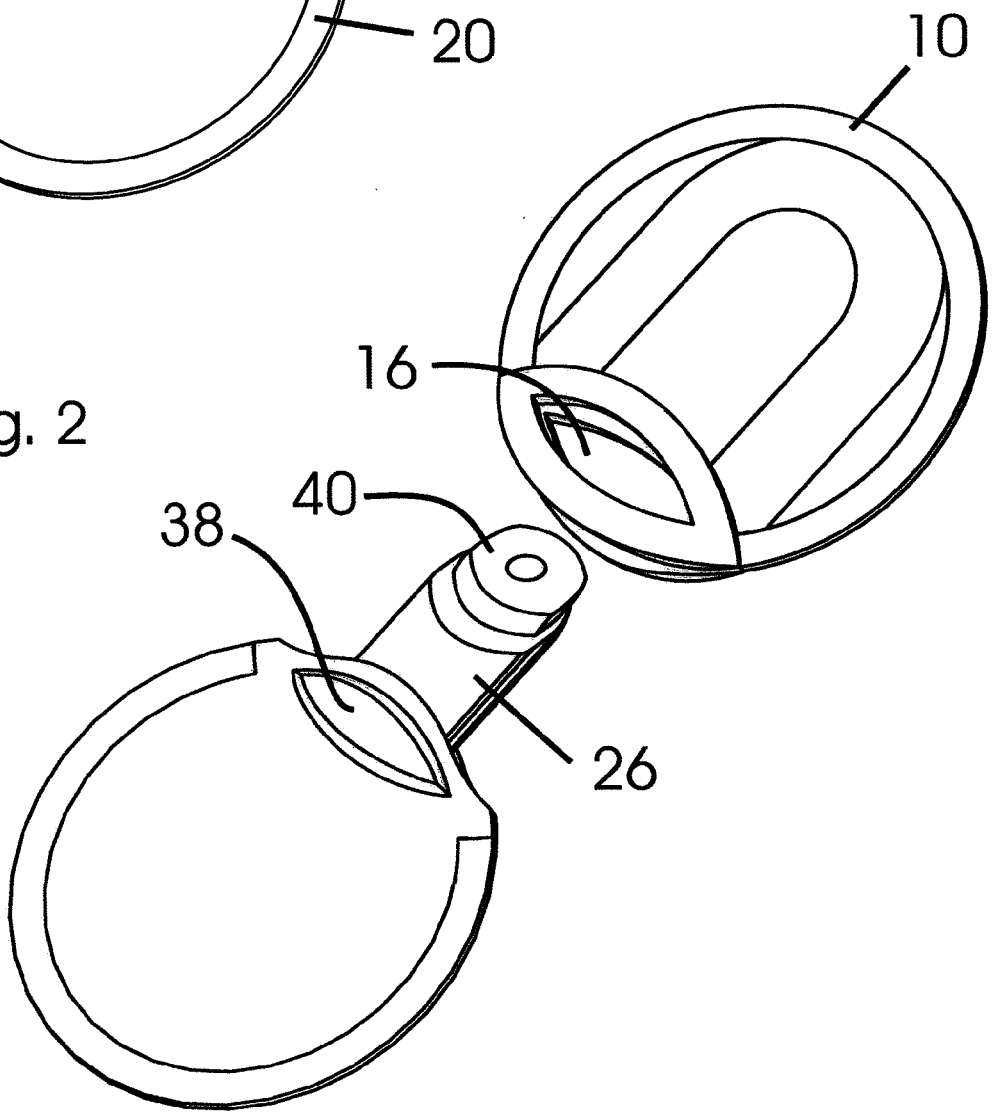
FIG. 2 shows an isometric view of the dispenser of FIG. 1, with the filled vessel open due to separation from the cap.

Turning to FIGS. 1 and 2, a cap 10 covers and seals an applicator tip 26 that extends from a vessel or fluid container

20. The cap 10 is molded with a lateral hole 16 that mates with a correspondingly shaped lug 38 when the cap 10 is in the closed position and assists in retaining the cap 10. Turning to FIG. 3, the mating structure for the applicator tip 26 and cap 10 includes a stopper 12 and a sealing bead 18 that cooperate with each other in the mated condition to seal the applicator tip 26 by the cap 10. To effectuate this, the stopper 12 passes through an opening in the compliant surface 40 to reach the mated condition. The cap 10 has the stopper 12 and the applicator tip 26 has the sealing bead 18.

An applicator tip 26 is elongated to terminate at a distal end where there is a porous and compliant surface 40, which may be of a foam or sponge material. The compliant surface 40 is used to evenly apply the whitening compound 44 (FIG. 3) to the tooth surfaces being treated and can additionally be used to gently scrub the tooth surface.

In FIG. 3, the stopper 12 passes through the porous and compliant surface 40 to seal a fluid passage 32 that projects outwardly from a body of the vessel or fluid container 20. A sealing bead 18 provides an annular type seal with the cap 10 to prevent leakage of the contents of the vessel or fluid container 20.

Turning to FIG. 4, the vessel or fluid container 20 may be squeezed in the direction indicated by arrows F, although such squeezing may occur at other areas and does not require pressure from two opposite sides or areas; pressure on one side or area may also be sufficient. A whitening compound 44 (or, for other applications, the corresponding compound) is urged through the fluid passage 32 and through the passage 48 of the applicator tip 26, where the whitening compound 44 mixes with sodium bicarbonate, producing a reactant 46 that becomes accessible on the porous and compliant surface 40.

Referring to FIG. 5, it can be seen that the vessel or fluid container 20 is able to flatten under manual squeezing pressure, allowing almost all of the contents to be expelled from the interior volume 50. The sides 56 conform closely to the contours of bulkhead 52. There are lugs 38 that act to further force remaining fluid from the vessel interior 50.

FIG. 6 shows a bulkhead 52 attaching applicator tip 26 to fluid container sides 56, having a wedge shape, allowing said sides 56 to drape.

Turning to FIGS. 7 and 8, opposite end views of the vessel or fluid container 20 with applicator tip 26 are depicted. Sides 56 (FIG. 6) come to a sharp seam without sidewalls, allowing them to collapse flat.

Figure 9:
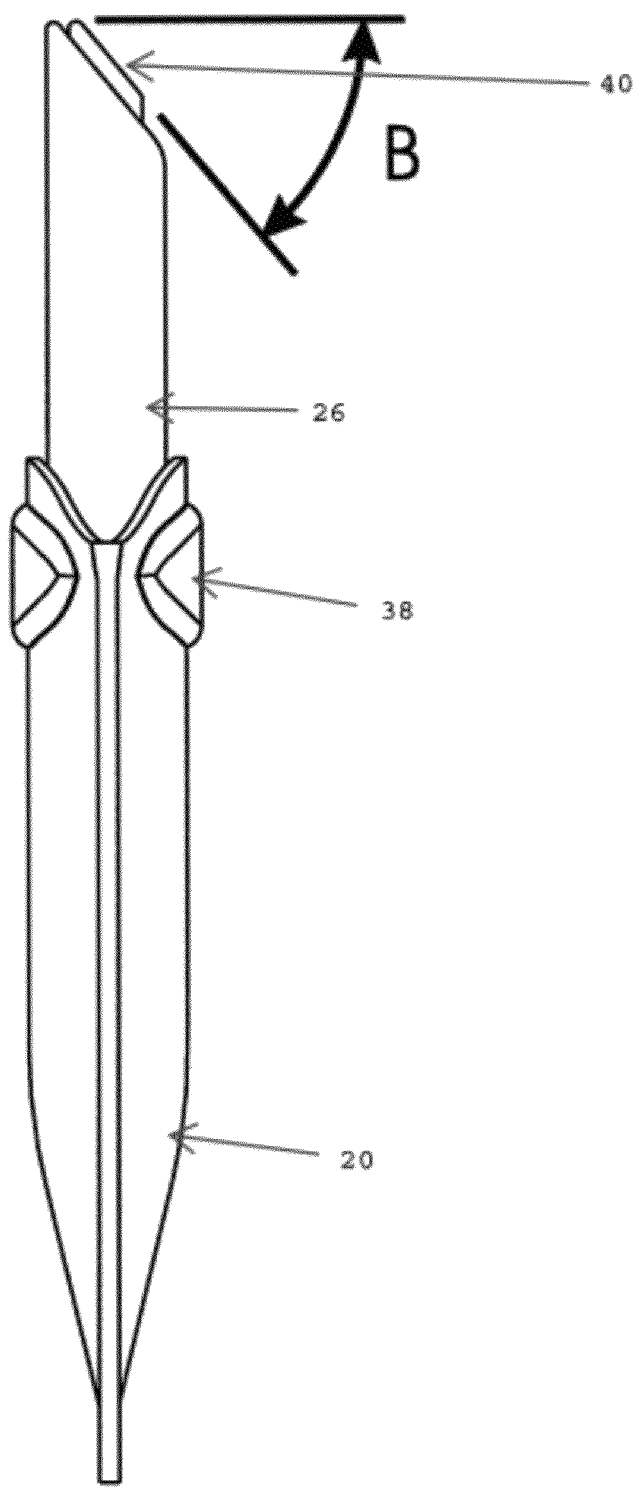
FIG. 9 shows a side view of the filled vessel and applicator tip of FIG. 4 to illustrate the angle of inclination of the compliant tip.

Turning to FIG. 9, an angle of inclination B of the compliant surface 40 is preferably within a range of 30° to 45° for optimal application of the activated reactants on the compliant surface 40. That is, the reactants become active by squeezing on the surface, thereby causing the whitening compound contents (e.g., hydrogen peroxide or other contents for other applications) to move within the vessel or fluid container 20 through the applicator tip 26 and to deposit onto the impregnated absorbent, compliant surface 40 (impregnated with sodium bicarbonate, baking soda or other substrates for other applications).

If desired, additional ingredients may be added, such as ingredients suited to polish teeth, for added benefit.

Figures 10, 11:
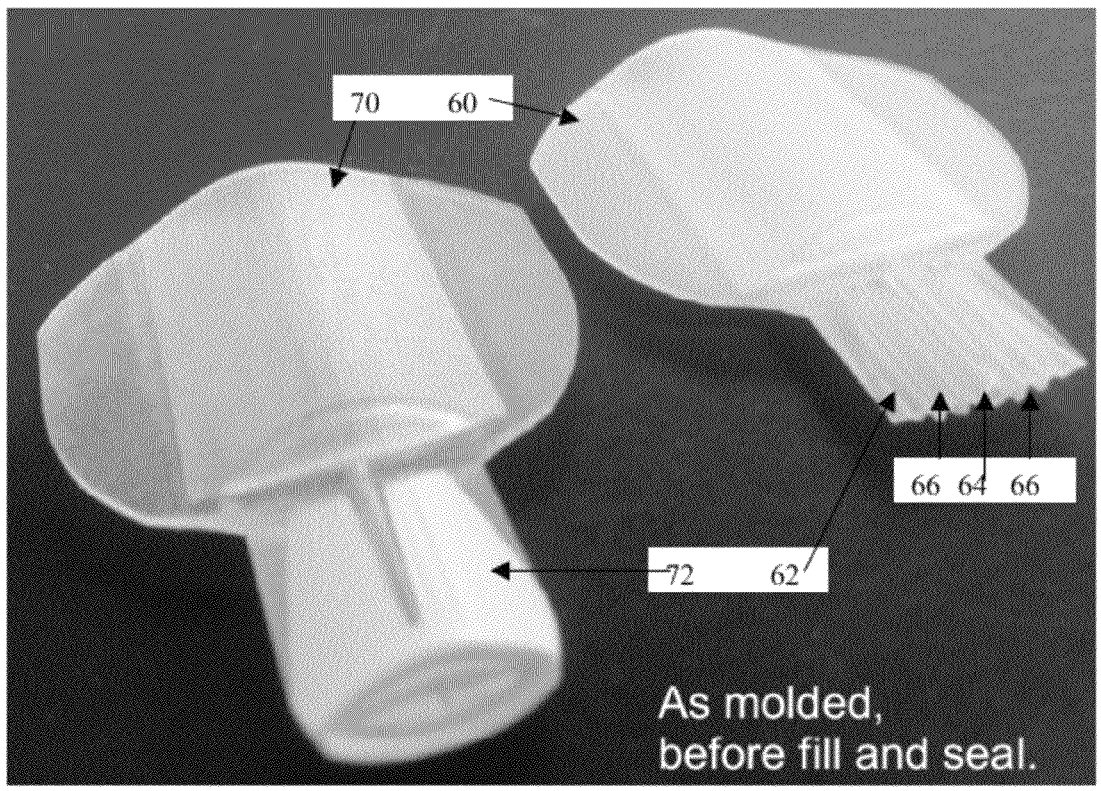
FIG. 10 shows an isometric view of an empty vessel in accordance with a further embodiment of the present invention.
FIG. 11 shows an isometric view of the empty vessel of FIG. 10 with a soft, elastomeric application tip.
Figures 12, 13:
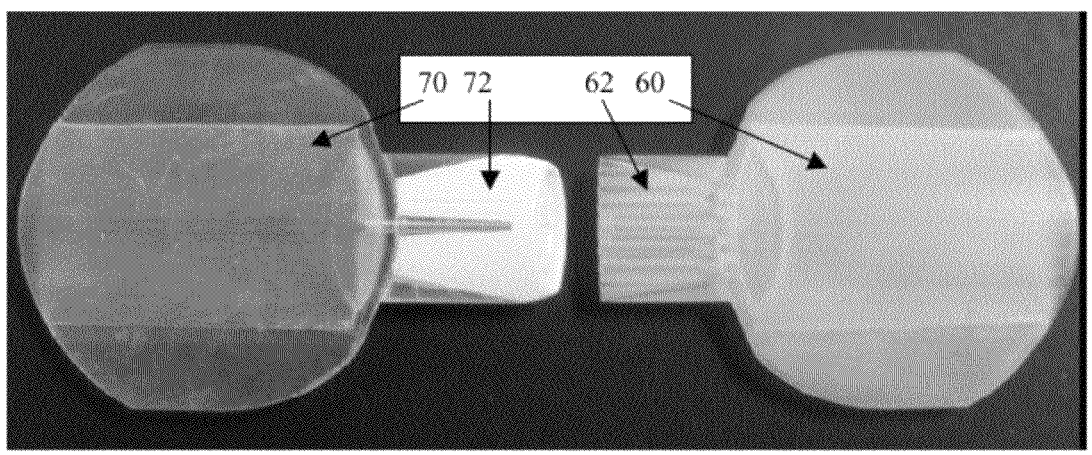
FIG. 12 shows a top plan view of the empty vessel of FIG. 10.
FIG. 13 shows a top plan view of the empty vessel with the soft, elastomeric application tip of FIG. 11.
Figure 20:
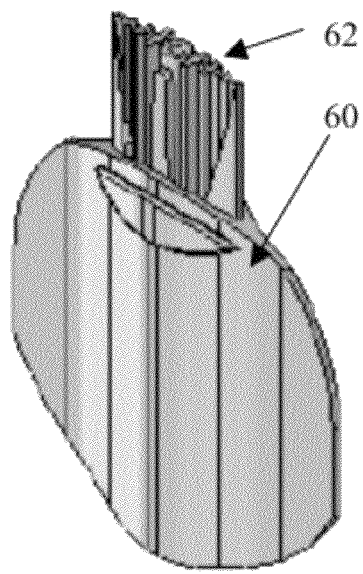
FIG. 20 shows an isometric view of the vessel of FIG. 14.
Figure 21:
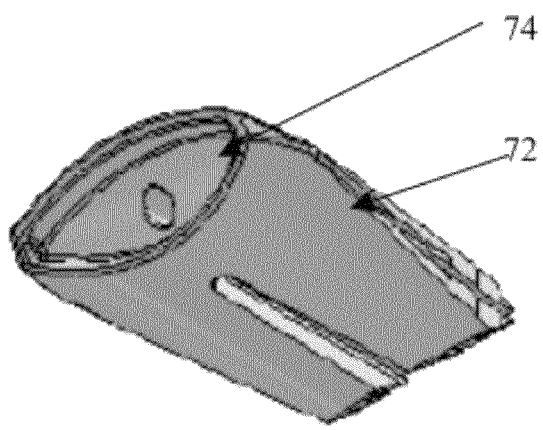
FIG. 21 shows an isometric view of the soft, elastomeric application tip of FIGS. 11 and 13.
Figure 22:
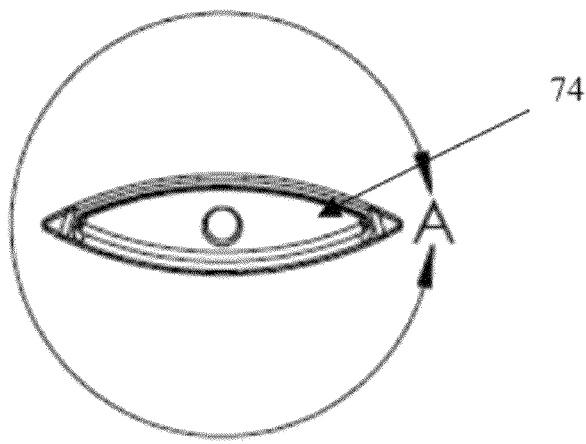
FIG. 22 shows a front view of the soft, elastomeric application tip of the embodiment of FIG. 21.
Figure 23:
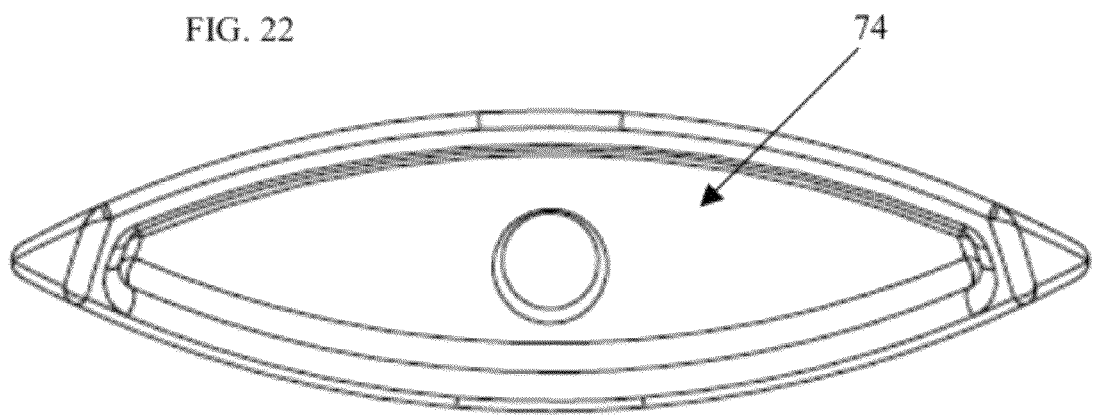
FIG. 23 shows a detailed view of FIG. 22.

Turning to FIGS. 10 and 12, a further embodiment of a dispenser is depicted that includes a vessel 60 that has an integrally formed rigid substructure 62. Turning to FIGS. 11 and 13, a dispenser 70 is shown that includes the vessel 60 of FIGS. 10 and 12 and includes a contoured, soft, elastomeric application tip 72 that is fitted over or with the rigid substructure 62. The contoured, soft, elastomeric application tip 72 allows for squeegee like, even spreading of the gel over the tooth surfaces and its softness helps prevent injury to the gums or teeth (or skin, etc. for other applications) that is more apt to occur with harder material.

The rigid substructure 62 may be elongated with a central tube 64 that extends in a direction of elongation of the rigid substructure 62. On both sides may be formed a series of spaced apart channels 66 that likewise extend in a direction of elongation of the rigid substructure 62 substantially parallel to each other.

Turning to FIGS. 13-14, the structure of the vessel 60 can be seen in greater detail. The rigid structure 62 preferably widens toward the central tube 64 from the opposite ends to define an elliptical outline broken by the spaced apart channels 66 (see FIG. 19). Turning to FIGS. 21-27, the structure of the contoured, soft, elastomeric application tip 72 can be seen in greater detail. The contoured, soft, elastomeric application tip 72 includes a recess 74 at one end and a slot 76 that spaces two symmetric legs 78 apart from each other. The shape of the contoured, soft, elastomeric application tip 72 may be such that it diverges outwardly from the recess 74 to a location near the recess and then converges or tapers along the symmetric legs 78 until termination. The symmetric legs may each have grooves 79 spaced apart from each other. FIGS. 28-33 show the dispenser 70 in greater detail when closed by a cap 80. The cap 80 may be formed with structures that complement the symmetric legs 78 and slot 76 of FIG. 25 so as to engage and seal off the dispenser 70.

Figure 34:
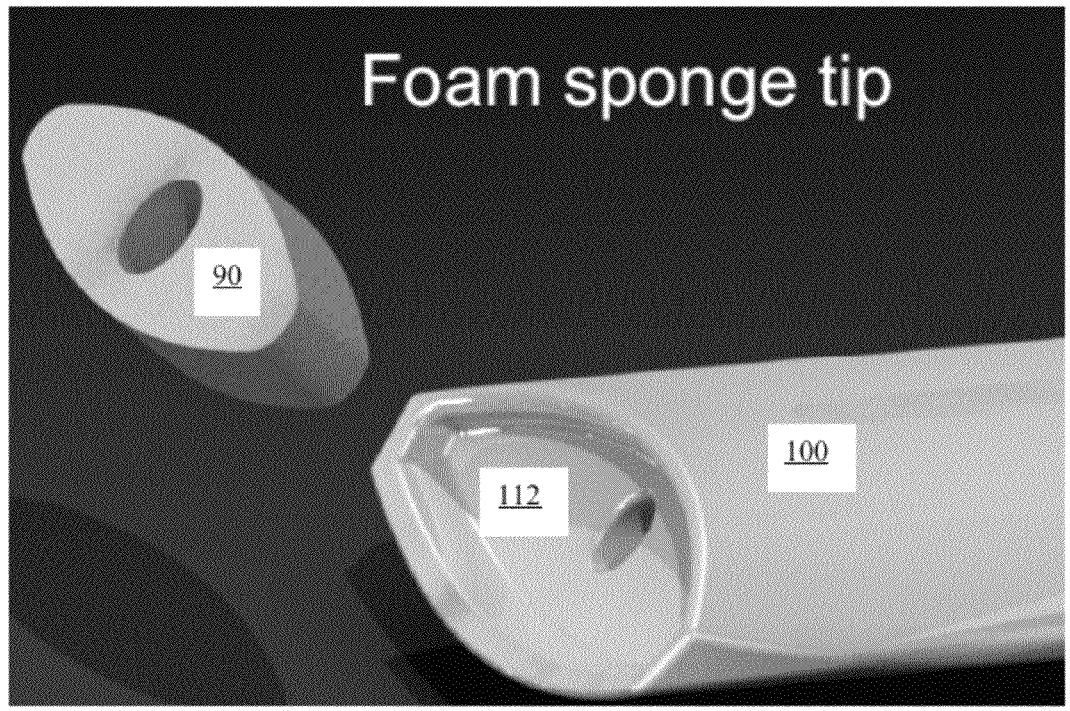
FIG. 34 shows an isometric view of a foam sponge application tip in accordance with the invention with a foam sponge tip (shown prior to inserting the foam sponge into a recess).
Figure 35:
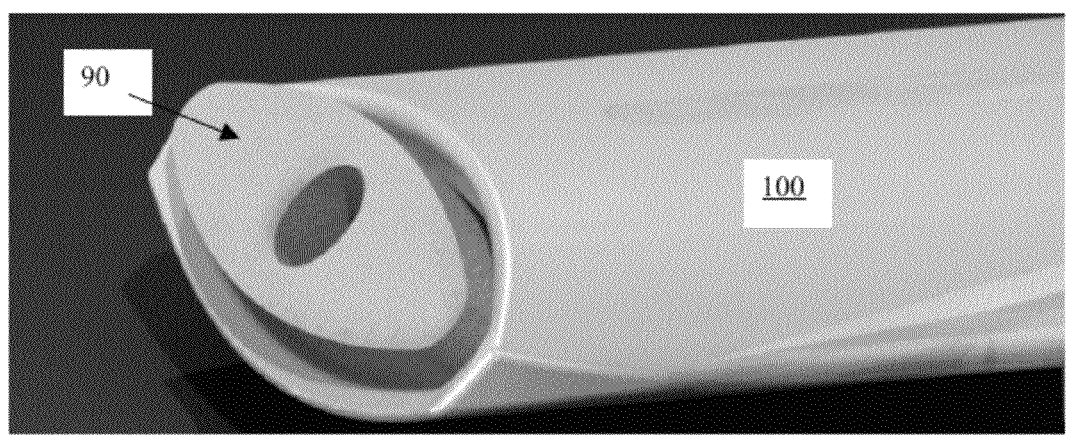
FIG. 35 shows an isometric view of the foam sponge application tip embodiment of FIG. 34 after the foam sponge is inserted into the recess.

Referring to FIGS. 34-35, a preferred embodiment is depicted for attaching a bicarbonate of soda treated sponge foam pad 90 to the tip 100. The sponge foam pad 90 is formed of a die cut open cell foam rubber that has been dipped in a solution of bicarbonate of soda and allowed to dry. This treated sponge foam pad 90 is then attached to a recess 112 at an end of the tip 100 with adhesive or heat sealing. The sponge foam pad 90 holds a quantity of treated gel at the tip 100 during application without having the gel drain or slide off. This allows for thicker, more even coating.

Figures 36, 37:
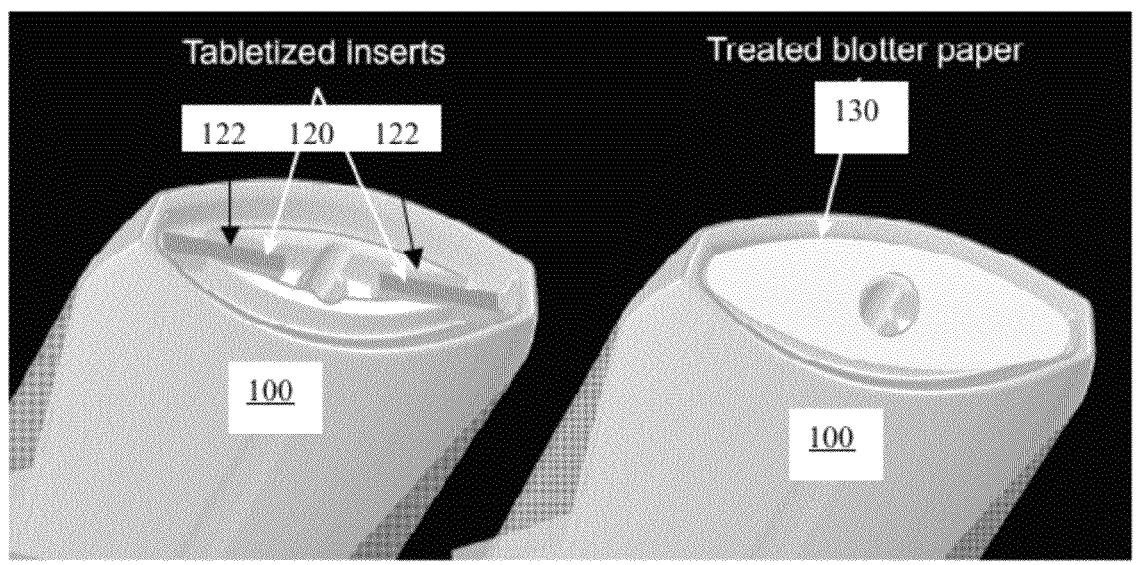
FIG. 36 shows an isometric view of an application tip in accordance with the invention having tabletized inserts.
FIG. 37 shows an isometric view of application tip in accordance with the invention having treated blotter paper.

Alternately, as seen in FIG. 36, the tip 100 can have additional ribbing in the form of tabletized inserts 120, which captures powdered or tabularized bicarbonate of soda. The tabletized inserts 120 are fitted into complementary-shaped channels 122 in the end of the tip 100.

Alternatively, treated blotter paper material 130 (see FIG. 37) can replace the sponge material of the sponge foam pad 90 of FIGS. 34-35 at the tip 100. This provides a means of capturing larger amounts of powder in the grooves of the tip by sealing to the perimeter, thereby forming a cover.

Figure 38:
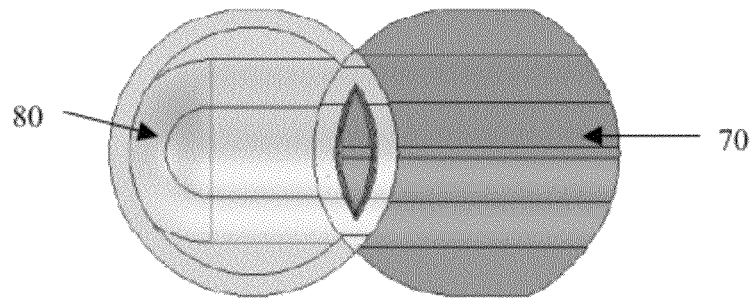
FIGS. 38-40 are progressive top views showing a capped dispenser in accordance with the invention assembled ready for fill, heat sealed and trimmed for the finished product, respectively.
Figure 39:
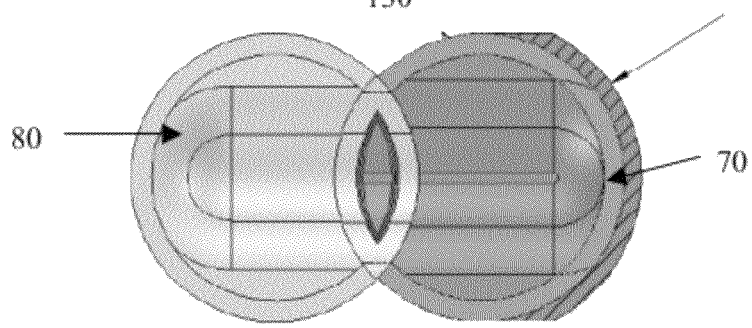
Figure 40:
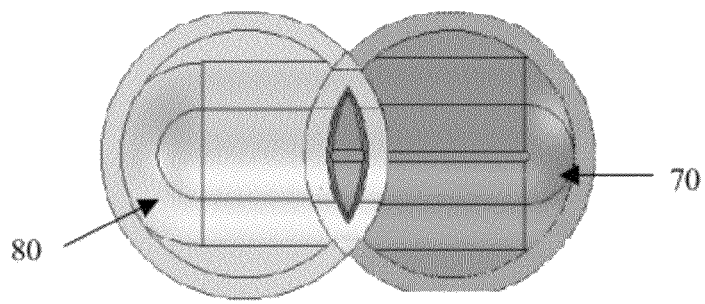

FIGS. 38-40 show a progression of views for filling the dispenser 70 with contents to be dispensed. Initially, the dispenser 70 and cap 80 are formed separately, with the dispenser 70 being open at opposite ends. One of the open ends is closed and sealed by cap 80. Thus, the assembly is ready to be filled as in FIG. 38. After filling the dispenser through the open end with contents to be dispensed, the opening is closed by heat sealing inwardly from the periphery (within heat seal area 130) in the manner of FIG. 39. The portion of the dispenser between the heat seal and the periphery may be trimmed off (trim area 132) to yield the finished product of FIG. 40.

As stated above, the applicator of the present invention may be used other than for teeth whitening or polishing. For instance, the following applications are contemplated: dermatological applications by delivering skin treatment applications; adhesives, such as epoxies, sealants, pharmaceutical treatments, remedies and drugs; naturopathic applications; and many others.

While the foregoing description and drawings represent the preferred embodiments of the present invention, it will be understood that various changes and modifications may be made without departing from the spirit and scope of the present invention.

What is claimed is:

1. An apparatus for dispensing contents, comprising a dispenser that includes an applicator tip with an elastomeric accommodating surface, a vessel having walls that contain contents, and a fluid passage from an interior of the vessel through the applicator tip to the accommodating surface, the walls configured to squeeze together under force from a non-flattened condition into a flattened condition to urge the contents to leave the vessel and pass through the fluid passage to reach the accommodating surface of the applicator tip provided the fluid passage is open, the walls being spaced further away from each other in the non-flattened condition than in the flattened condition, and mating structures arranged to mate with each other to close and seal the fluid passage until the mating structures are separated from each other to open the fluid passage, said vessel having a distal end portion formed as a rigid substructure that supports said elastomeric surface, said rigid substructure being elongated with opposite sides each with a series of spaced apart channels that extend in a direction of elongation of the rigid substructure and substantially parallel to each other.

2. The dispenser of claim 1, wherein the applicator tip is elongated, the accommodating tip defining an angle of approximately 30° to 45° relative to a direction of elongation of the applicator tip.

3. The dispenser of claim 1, wherein the accommodating surface is porous.

4. The dispenser of claim 3, wherein the accommodating surface is a reactive material that reacts with the contents upon contact.

5. The dispenser of claim 3, wherein the accommodating surface covers a chamber, the chamber holding a particular material, the vessel containing a different material that reacts with the particular material held in the chamber upon contact.

6. The dispenser of claim 1, wherein the mating structures include a stopper and a sealing bead that cooperate with each other in a mated condition to seal the fluid passage, the stopper passing through an opening in the accommodating surface to reach the mated condition.

7. The dispenser of claim 1, wherein the rigid substructure has a central tube that is elongated to extend in the direction of elongation of the rigid substructure, the series of channels includes two sets each separated from each other by the central tube and each being configured and arranged so as to be symmetric with each other.

8. The dispenser of claim 1, wherein the applicator tip has one end with a recess, the elastomeric surface being part of a component that is within the recess.

9. The dispenser of claim 8, wherein the component is a foam sponge pad that has the elastomeric surface.

10. The dispenser of claim 1, wherein the applicator tip has a recess, further comprising a foam sponge pad at least partially within the recess.

11. The dispenser of claim 1, wherein the applicator tip has a recess, further comprising tabletized inserts that are at least partially within the recess.

12. The dispenser of claim 1, wherein the applicator tip has a recess, further comprising treated blotter paper at least partially within the recess.

13. The dispenser of claim 1, wherein the dispenser has a portion having a heat seal construction.

14. The dispenser of claim 1, wherein the applicator tip is elongated with a recess at one end and two legs at another end, the two legs being separated from each other by a slot.

15. The dispenser of claim 14, wherein the two legs have ends with grooves spaced from each other.

16. The dispenser of claim 4, wherein the reactive material and the contents are suitable for whitening teeth upon contact with each other.

17. The dispenser of claim 4, wherein the reactive material and the contents are suitable for polishing teeth upon contact with each other.

18. The dispenser of claim 4, wherein the reactive material and the contents are suitable for dermatological applications.

19. The dispenser of claim 4, wherein the reactive material and the contents are suitable for adhesive applications.

20. An apparatus suited to dispense contents, comprising means for dispensing that includes an applicator tip with an accommodating surface, vessel means for containing contents and that has walls, and fluid passage means extending from an interior of the vessel through the applicator tip to the accommodating surface for channeling the contents to the accommodating surface, the walls being configured to squeeze together under manual force from a non-flattened condition into a flattened condition to urge the contents to leave the vessel means to pass through the fluid passage means to reach the accommodating surface of the applicator tip provided the fluid passage is open, the walls being spaced further away from each other in the non-flattened condition than in the flattened condition, and means for closing and sealing the fluid passage means that includes mating structures arranged to mate with each other to close and seal the fluid passage until the mating structures are separated from each other to open the fluid passage, said accommodating surface being an elastomeric surface, said vessel having a distal end portion formed as a rigid substructure, said elastomeric surface being supported by the rigid substructure, said applicator tip having one end with a recess, said elastomeric surface being part of a component that is within the recess.

21. The dispenser of claim 20, wherein the applicator tip is elongated, the accommodating tip defining an angle between 30° and 45° inclusive relative to a direction of elongation of the applicator tip.

22. The dispenser of claim 20, wherein the accommodating surface is porous.

23. The dispenser of claim 21, wherein the accommodating surface has a reactive means for reacting with the contents upon contact.

24. The dispenser of claim 23, wherein the accommodating surface covers a chamber, the chamber holding a particular material, the vessel containing a different means for reacting with the particular material held in the chamber upon contact therewith.

25. The dispenser of claim 20, wherein the mating structures include a stopper and a sealing bead that cooperate with each other in a mated condition to seal the fluid passage, the stopper passing through an opening in the accommodating surface to reach the mated condition, a cap.

26. The dispenser of claim 20, wherein the rigid substructure is elongated with opposite sides each with a series of spaced apart channels that extend in a direction of elongation of the rigid substructure and substantially parallel to each other.

27. The dispenser of claim 20, wherein the rigid substructure has a central tube that is elongated to extend in the direction of elongation of the rigid substructure, the series of channels includes two sets each separated from each other by the central tube and each being configured and arranged so as to be symmetric with each other.

28. The dispenser of claim 20, wherein the component is a foam sponge pad that has the elastomeric surface.

29. The dispenser of claim 20, wherein the applicator tip has a recess, further comprising a foam sponge pad at least partially within the recess.

30. The dispenser of claim 20, wherein the applicator tip has a recess, further comprising tabletized inserts that are at least partially within the recess.

31. The dispenser of claim 20, wherein the applicator tip has a recess, further comprising treated blotter paper at least partially within the recess.

32. The dispenser of claim 20, wherein the dispenser has a portion having a heat seal construction.

33. The dispenser of claim 20, wherein the applicator tip is elongated with a recess at one end and two legs at another end, the two legs being separated from each other by a slot.

34. The dispenser of claim 33, wherein the two legs have ends with grooves spaced from each other.

35. The dispenser of claim 23, wherein the reactive means and the contents are medically suited for whitening teeth upon contact with each other.

36. The dispenser of claim 23, wherein the reactive means and the contents are medically suited for polishing teeth upon contact with each other.

37. The dispenser of claim 23, wherein the reactive means and the contents are dermatologically suited for application onto skin blemishes upon contact with each other.

38. The dispenser of claim 4, wherein the vessel contains a tooth whitening gel.

39. An apparatus suited to dispense contents, comprising means for dispensing that includes an applicator tip with an accommodating surface, vessel means for containing contents and that has walls, and fluid passage means extending from an interior of the vessel through the applicator tip to the accommodating surface for channeling the contents to the accommodating surface, the walls being configured to squeeze together under manual force from a non-flattened condition into a flattened condition to urge the contents to leave the vessel means to pass through the fluid passage means to reach the accommodating surface of the applicator tip provided the fluid passage is open, the walls being spaced further away from each other in the non-flattened condition than in the flattened condition, and means for closing and sealing the fluid passage means that includes mating structures arranged to mate with each other to close and seal the fluid passage until the mating structures are separated from each other to open the fluid passage, the accommodating surface being an elastomeric surface, the vessel having a distal end portion formed as a rigid substructure, the elastomeric surface being supported by the rigid substructure, said rigid substructure being elongated with opposite sides each with a series of spaced apart channels that extend in a direction of elongation of the rigid substructure and substantially parallel to each other.

40. An apparatus suited to dispense contents, comprising means for dispensing that includes an applicator tip with an accommodating surface, vessel means for containing contents and that has walls, and fluid passage means extending from an interior of the vessel through the applicator tip to the accommodating surface for channeling the contents to the accommodating surface, the walls being configured to squeeze together under manual force from a non-flattened condition into a flattened condition to urge the contents to leave the vessel means to pass through the fluid passage means to reach the accommodating surface of the applicator tip provided the fluid passage is open, the walls being spaced further away from each other in the non-flattened condition than in the flattened condition, and means for closing and sealing the fluid passage means that includes mating structures arranged to mate with each other to close and seal the fluid passage until the mating structures are separated from each other to open the fluid passage, said accommodating surface being an elastomeric surface, said vessel having a distal end portion formed as a rigid substructure, said elastomeric surface being supported by the rigid substructure, and further wherein the rigid substructure has a central tube that is elongated to extend in the direction of elongation of the rigid substructure, the series of channels includes two sets each separated from each other by the central tube and each being configured and arranged so as to be symmetric with each other.

* * * * *